(12) United States Patent
Zhang et al.

(10) Patent No.: US 10,813,813 B2
(45) Date of Patent: Oct. 27, 2020

(54) LOCALIZED TOPICAL HYPERBARIC THERAPEUTIC INSTRUMENT

(71) Applicant: Baoding Baienjie biotechnology Co. Ltd., Baoding (CN)

(72) Inventors: Liping Zhang, Baoding (CN); Jinhua Zhang, Baoding (CN)

(73) Assignee: Baoding Baienjie Biotechnology Co., Ltd., Baoding (CN)

( * ) Notice: Subject to any disclaimer, the term of this patent is extended or adjusted under 35 U.S.C. 154(b) by 612 days.

(21) Appl. No.: 15/488,453

(22) Filed: Apr. 15, 2017

(65) Prior Publication Data
US 2018/0147102 A1    May 31, 2018

(30) Foreign Application Priority Data

Nov. 29, 2016 (CN) .......................... 2016 1 1090078

(51) Int. Cl.
| | |
|---|---|
| *A61G 10/02* | (2006.01) |
| *A61M 16/10* | (2006.01) |
| *A61H 1/00* | (2006.01) |
| *A61H 9/00* | (2006.01) |
| *A61M 35/00* | (2006.01) |
| *A61M 37/00* | (2006.01) |

(52) U.S. Cl.
CPC .......... *A61G 10/026* (2013.01); *A61H 1/008* (2013.01); *A61H 9/0078* (2013.01); *A61M 16/1005* (2014.02); *A61M 35/00* (2013.01); *A61M 37/00* (2013.01); *A61G 2203/34* (2013.01); *A61H 2201/0103* (2013.01); *A61H 2201/0207* (2013.01); *A61H 2201/5056* (2013.01); *A61H 2201/5071* (2013.01)

(58) Field of Classification Search
CPC . A61G 10/026; A61G 7/05776; A61M 16/10; A61M 16/1005; A61M 35/30; A61M 37/00; A61H 9/0078
USPC ........ 261/142; 601/148, 149, 150, 151, 152; 602/13; 422/125
See application file for complete search history.

(56) References Cited

U.S. PATENT DOCUMENTS

| | | | | |
|---|---|---|---|---|
| 4,634,179 A | * | 1/1987 | Hashimoto | ............ A47C 7/467 297/284.3 |
| 4,869,853 A | * | 9/1989 | Chen | ......................... F22B 1/28 261/142 |

(Continued)

*Primary Examiner* — Samchuan C Yao
*Assistant Examiner* — Vincent D Hoang
(74) *Attorney, Agent, or Firm* — CBM Patent Consulting, LLC (57) ABSTRACT

A localized topical hyperbaric therapeutic instrument, comprising: a primary airbag, which is a chamber with an opening at an end; an oxygen generating device, which comprises an oxygen generator and a first pressure controller, wherein the oxygen generator has an oxygen outlet which communicates with the primary airbag through a first air inlet line and supplies oxygen into the primary airbag, and wherein the first pressure controller controls an amount of oxygen supplied to the primary airbag by the oxygen generator; a massage device; a heating piece, which is arranged in the primary airbag and generates heat; a treatment unit, which is arranged in the primary airbag in a detachable manner, disposed at a position corresponding to the heating piece, and comprises medical ingredients which are volatile upon heating.

15 Claims, 4 Drawing Sheets

(56) References Cited

U.S. PATENT DOCUMENTS

| | | | | |
|---|---|---|---|---|
| 6,321,746 | B1* | 11/2001 | Schneider | A61G 10/026 128/202.12 |
| 6,484,716 | B1* | 11/2002 | Leininger | A61G 10/026 128/202.12 |
| 7,922,678 | B2* | 4/2011 | Hovorka | A61H 9/0078 602/13 |
| 8,454,542 | B2* | 6/2013 | Hirata | A61F 5/05816 601/150 |
| 2006/0161081 | A1* | 7/2006 | Barak | A61F 5/012 601/151 |
| 2006/0185670 | A1* | 8/2006 | Loori | A61M 35/30 128/202.12 |
| 2009/0214393 | A1* | 8/2009 | Chekal | B01D 53/047 422/120 |

* cited by examiner

FIG. 1

FPC: first pressure controller; PA: primary airbag; MA: massage airbag; TSV: two-way solenoid valve; SPS: second pressure sensor; SPC: second pressure controller; FPS: first pressure sensor; FSV: first one-way solenoid valve; SGF: second gas flux limiter; OFD: oxygen filtering device; HR: heat radiator; OID: oxygen inhaling device; AFD: air filtering device; HMD: humidifier; FGF: first gas flux limiter; MSC: molecular sieve absorption column; ACD: air compressing device; OT: oxygen tank; SSV: second one-way valve; AIE: air inlet end

LOCALIZED TOPICAL HYPERBARIC THERAPEUTIC INSTRUMENT

TECHNICAL FIELD

The present disclosure relates to the field of medical appliances, and particularly to a localized topical hyperbaric therapeutic instrument.

BACKGROUND

Hyperbaric anion oxygen treatment is also referred to as "hyperbaric oxygen treatment" or "hyperbaric oxygen treatment", and abbreviated as HBO. It refers to a therapeutic measure in an ecological level, which promotes the self-renewal process of a human body and enhances the vitality of immune cells, and has excellent therapeutic effects on central nervous poisoning, lung poisoning, emphysematous gangrene, diabetic foot, and various traumas. The diabetic foot is one of the most common complications of diabetes. Once a patient is attacked by such a disease, it poses a greater threat to the patient's feet. Each year about twenty percent of diabetic foot patients are amputated for this reason. As for treatment of the diabetic foot, attention should firstly be paid to the primary disease, to continuously improve blood supply for the lower limbs and control the level of blood glucose. As for patients at an early stage of diabetic foot, drug therapy with diuretic and local application to the wound is adopted. It is clinically proven that hyperbaric oxygen treatment has favorable effects on the healing of the diabetic foot.

However, the existing oxygen treatment apparatus is generally a bulky hyperbaric oxygen chamber. The patient is required to get his whole body into the chamber. The oxygen chamber is operated by professionals, and the treatment cost is high. Improper operation during treatment will cause serious consequences such as oxygen poisoning, dysbaric injury and decompression sickness. This is adverse for local treatment of the diabetic foot, emphysematous gangrene, and local trauma of limbs. Although a portable hyperbaric oxygen chamber has been reported, the patient is also generally required to get his whole body into a closed oxygen environment, which similarly brings about unfavorable factors.

The application CN98814069.1, entitled "Shape-adaptable topical hyperbaric oxygen chamber" discloses a bag applicable to a topical hyperbaric oxygen treatment. The bag has an outlet through which the patient gets his body or a portion thereof into bag. The bag is shrunk at the outlet in the form of pleats, so that the bag is sealed. However, there is no pressure control system in the bag. Pleats are arranged at the outlet and the entire body of the bag, so that an ideal value of pressure and thus effective therapeutic effects cannot be reached. The oxygen value of pressure in the bag is larger than the atmospheric pressure by 5-10 mm of mercury (mm of Hg). According to literature, the pressure in this range cannot offer effective oxygen therapeutic effects. Therefore, it is urgent to develop a device or apparatus which can effectively apply hyperbaric oxygen treatment to local treatment of limbs.

SUMMARY

It is an object of the present disclosure to at least solve the above problems, and at least provide advantages which will be described hereinafter.

It is another object of the present disclosure to provide a localized topical hyperbaric therapeutic instrument, which can apply effective hyperbaric oxygen treatment to a local portion of the patient, which is safe and convenient to use, and which provides excellent therapeutic effects.

It is a further object of the present disclosure to provide a localized topical hyperbaric therapeutic instrument which further has a massage function, and combines the massage function with the hyperbaric oxygen treatment to improve therapeutic effects of hyperbaric oxygen.

It is yet another object of the present disclosure to provide a localized topical hyperbaric therapeutic instrument which combines hyperbaric oxygen treatment, massage function, thermal therapy and Chinese herbs fumigation integrally, and can effectively improve quality and effect.

In order to realize these objects and other advantages of the present disclosure, the present disclosure provides the following technical solutions.

A localized topical hyperbaric therapeutic instrument comprises:

a primary airbag, which is a chamber with an opening at an end, wherein the opening is provided with a sealing part;

an oxygen generator, which comprises an oxygen generator and a first pressure controller, wherein the oxygen generator generates oxygen and has an oxygen outlet, and the oxygen outlet communicates with the primary airbag through a first air inlet line and supplies oxygen into the primary airbag, and wherein the first pressure controller controls an amount of oxygen supplied to the primary airbag by the oxygen generator, and keeps a value of gas pressure in the primary airbag in a range of 1 KPa-10 KPa;

a massage device, which comprises a massage airbag, an air pump and a second pressure controller, wherein the massage airbag is arranged on an inner wall of the primary airbag, the air pump communicates with the massage airbag through a second air line, and the second pressure controller is connected with the air pump and the massage airbag, respectively, so that the value of gas pressure in the massage airbag changes regularly between 0 and 20 KPa;

a heating piece, which is arranged in the primary airbag and generates heat; and a treatment unit, which is arranged in the primary airbag in a detachable manner, disposed at a position corresponding to the heating piece, and comprises medical ingredients which are volatile upon heating.

For example, a first pressure sensor, which detects a value of pressure in the primary airbag;

a first pressure controller, which is connected with the first pressure sensor, and receives a signal from the first pressure sensor;

a first one-way solenoid valve, which is arranged in the first air inlet line communicating the oxygen generator and the primary airbag, the first one-way solenoid valve is connected with the first pressure controller, and as a response to the received signal, the first pressure controller further controls opening and closing of the first one-way solenoid valve; and a venting system, which comprises an exhaust pipe communicating with the primary airbag and a second one-way solenoid valve arranged in the exhaust pipe, the second one-way solenoid valve is connected with the first pressure controller, and as a response to the received signal, the first pressure controller further controls opening and closing of the second one-way solenoid valve.

For example, a second pressure sensor, which detects a value of pressure in the massage airbag;

a second pressure controller, which is connected with the second pressure sensor, and receives a signal from the second pressure sensor; and a two-way solenoid valve, which is arranged in the second air line communicating the air pump and the massage airbag, the two-way solenoid valve is connected with the second pressure controller, and as a response to the received signal, the second pressure controller controls the two-way solenoid valve to inflate or vent the massage airbag.

For example, the massage airbag has a ring shape, the massage airbag has a number of 2 or more, and the massage airbags are arranged in parallel along the extending direction of the height of the primary airbags.

For example, the oxygen generator is a molecular sieve oxygen generator, and the molecular sieve oxygen generator comprises:

an air compressing device, wherein an air filtering device is arranged at an air inlet end of the air compressing device, for filtering the air which enters the air compressing device;

a molecular sieve absorption column, wherein the air compressing device communicates with an air inlet of the molecular sieve absorption column through the second air inlet line, and a heat radiator is arranged in the second air inlet line;

an oxygen tank, wherein the oxygen tank communicates with an air outlet of the molecular sieve absorption column, and receives and stores the oxygen generated by the molecular sieve absorption column; wherein the oxygen outlet is arranged in the oxygen tank; wherein an oxygen filtering device is arranged in the first air inlet line which communicates the oxygen outlet and the primary airbag, for filtering the oxygen which enters the primary airbag through the oxygen outlet.

For example, the localized topical hyperbaric therapeutic instrument further comprises an oxygen inhaling device, wherein the oxygen inhaling device and the primary airbag communicate in a parallel manner with the oxygen outlet or the first air inlet line, respectively;

a first gas flux limiter is arranged in a connecting passage between the oxygen inhaling device and the oxygen outlet or the first air inlet line.

For example, the treatment unit comprises an extract tablet 291 and a fixing part, the extract tablet 291 is arranged on a side of the heating piece close to the user's skin in a detachable manner through the fixing part; and the extract tablet 291 comprises Chinese herbs extract which is extracted from a Chinese herbs composition with an effect of promoting circulation and removing stasis, and the Chinese herbs composition comprises the following ingredients in weight parts:

Antongteng CAULIS CISSI 5-8, fiveleaf akebia fruit 8-12, Spreading Hedyotis Herb 5-8, Imperata cylindrica root 8-10, Angelica dahurica 8-10, Lobelia chinensis Lour 9-12, Liquidambar formosana Hance infructescence 6-8, myrrh 8-12, caulis sargentodoxae 8-10, Salvia miltiorrhiza 5-8, Rhodiola rosea 8-12, Caulis Spatholobi 8-10, Anoectochilus roxburghii 2-4, radix ranunculi ternati 2-4, flower buds of Radix Notoginseng 5-8, Garden Balsam Stem 8-12, Leonurus japonicus 8-10, pearl barley kernel 8-12, dandelion 8-12, and brazilwood 8-12.

For example, the heating piece is a far infrared heating piece; and wherein the fixing part comprises:

a panel, wherein the panel has a mesh shape, sticking hooks are arranged at crossings of the mesh, the panel has a curved surface with an adjustable curvature, and silica gel bumps with a height of 2-10 mm are arranged around the panel; and a connecting part, wherein the connecting part fixes the panel in the primary airbag, and the connecting part has an adjustable length, so that an inner side of the panel is spaced apart from the user's skin by 5-15 mm.

For example, the primary airbag is made from a flexible airtight material, the sealing part at the opening of the primary airbag comprises a first elastic sealing ring which is arranged on an inner wall of the primary airbag at the opening, and a second elastic sealing ring which is arranged outside the opening of the primary airbag, wherein the first elastic sealing ring is hollow, has a width of 3-10 cm, and expands in volume in an inflated state to decrease inner diameters of the elastic sealing rings, wherein one or more annular groove is arranged on the surface of the first elastic sealing ring in the inflated state; and the second elastic sealing ring is arranged outside the opening of the primary airbag, and is embedded in the annular groove of the first elastic sealing ring, so that the opening of the primary airbag is shrunken and sealed.

For example, the localized topical hyperbaric therapeutic instrument further comprises:

a box in which the oxygen generator and the air pump are arranged;

a control panel which is arranged in the box, wherein a first controller and a second controller are connected with the control panel, respectively; and a buzzer and timer which is connected with the control panel.

The present disclosure at least has the following beneficial effects.

Firstly, in the present disclosure, a closeable opening is arranged at an end of the primary airbag, and the primary airbag is connected with the oxygen generator and the pressure control system, so that a pure oxygen environment of 1 KPa-10 KPa can be maintained in the primary airbag. Hyperbaric oxygen in such a pressure range can sufficiently disperse into tissue cells through the naked wound, provide oxygen for the anoxic tissue cells, facilitate proliferation of fibrocyte and generation of collagen matrix, facilitate proliferation of tissue cells, inhibit and even kill anaerobic bacteria at deep wound, reduce generation of extracellular toxin, and accelerate the rehabilitation of the disease. Pressure beyond the above range cannot provide effective therapeutic effects. The user put his local portion of a limb into the primary airbag for hyperbaric oxygen treatment, so that it is safe and convenient to use, and provides excellent therapeutic effects.

Secondly, a massage airbag is arranged in the primary airbag of the present disclosure, so that the hyperbaric oxygen treatment is combined with a massage function. In this way, blood circulation is facilitated, proliferation of fibrocyte and generation of collagen matrix is facilitated, and effects of hyperbaric oxygen treatment are improved.

Thirdly, a heating piece and a treatment unit comprising volatile medicines are arranged in the primary airbag of the present disclosure. The heating piece heats the treatment unit at a close distance, so that the effective constituent of the medicines in the treatment unit volatilize and are absorbed by pores. In this way, the thermal therapy and the medicine fumigation treatment are effectively combined with the hyperbaric oxygen treatment, and individual therapeutic effects of hyperbaric oxygen treatment or medicine fumigation are significantly improved.

Other advantages, objects and features of the present disclosure will be either elucidated by the following text, or understood by the skilled in the art from studying and practicing the present disclosure.

DETAILED DESCRIPTION OF EMBODIMENTS

The specific embodiments of the present disclosure shall be further described in the following text with reference to the figures and the embodiments.

It is noted that the terms "contain", "include" and "comprise" as used herein does not exclude the presence or addition of one or more other elements or combination thereof.

As shown in FIG. 1-5, a localized topical hyperbaric therapeutic instrument comprises a primary airbag 1 which is a chamber with an opening at an end. The opening is provided with a sealing part 2. In the present disclosure, the primary airbag 1 is not limited to a certain shape. Other shapes for accommodating a portion of the body, shapes of the primary airbag after inflating, and shapes which are modified according to the portion of the body of interest fall within the scope of the present disclosure. The sealing part 2 can be elastic sealing strip, sealing ring, or other forms of tapes with an adjustable length for fastening. Once the patients get his limb to be treated (e.g. leg or arm) into the chamber, the primary airbag 1 is sealed by pulling the sealing part like the elastic sealing strip, so as to maintain the pressure of oxygen in the primary airbag 1.

Figure 1:
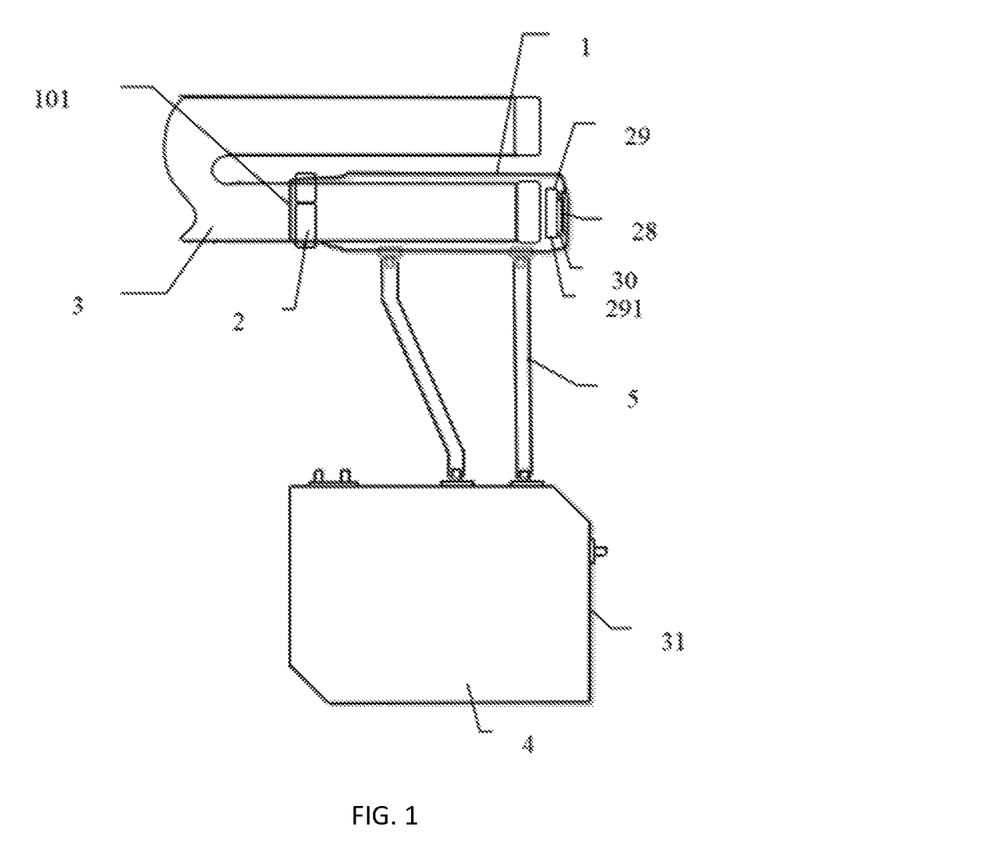
FIG. 1 is an overall structural view illustrating a localized topical hyperbaric therapeutic instrument of the present disclosure.
Figure 2:
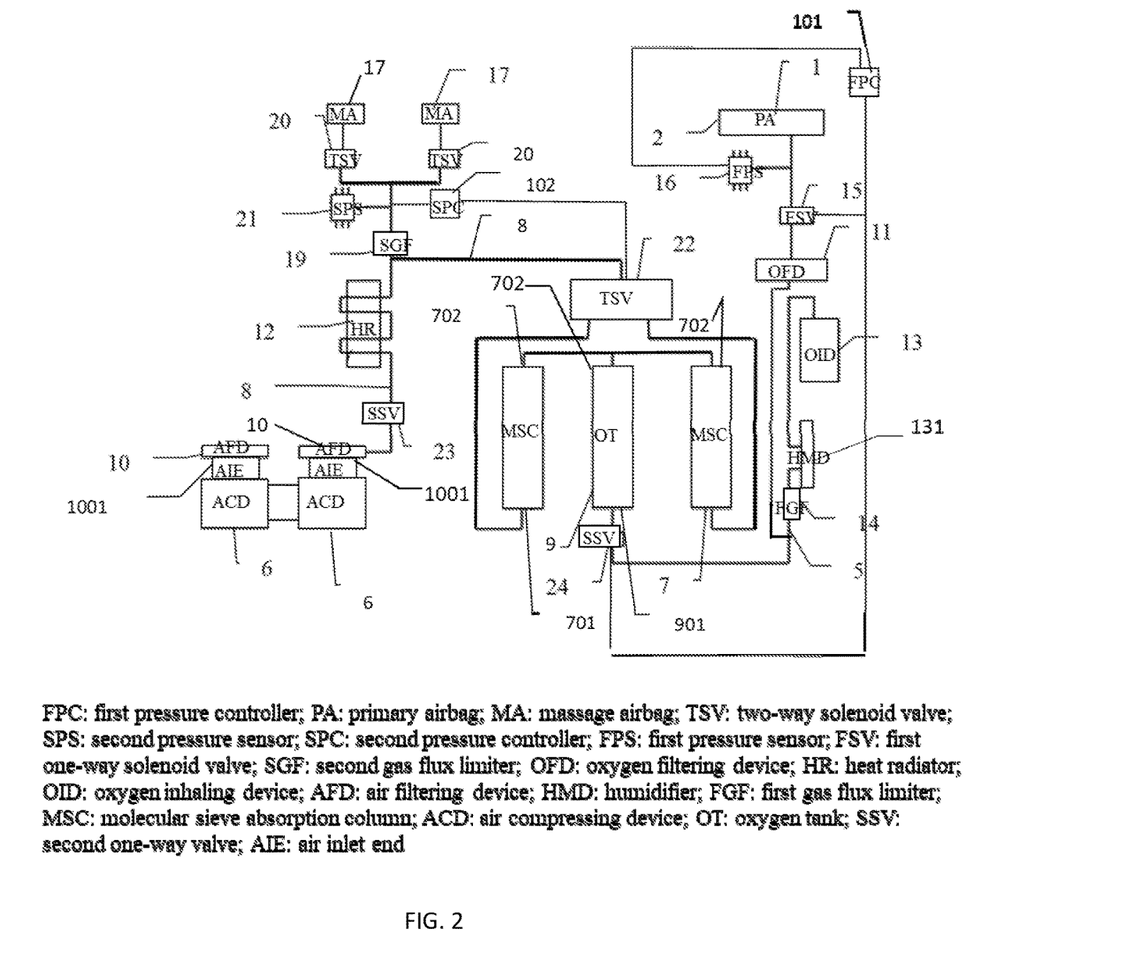
FIG. 2 is an overall connection view illustrating a localized topical hyperbaric therapeutic instrument of the present disclosure; FPC: first pressure controller; PA: primary airbag; MA: massage airbag; TSV: two-way solenoid valve; SPS: second pressure sensor; SPC: second pressure controller; FPS: first pressure sensor; FSV: first one-way solenoid valve; SGF: second gas flux limiter; OFD: oxygen filtering device; HR: heat radiator; OID: oxygen inhaling device; AFD: air filtering device; HMD: humidifier; FGF: first gas flux limiter; MSC: molecular sieve absorption column; ACD: air compressing device; OT: oxygen tank; SSV: second one-way valve; AIE: air inlet end.

The localized topical hyperbaric therapeutic instrument further comprises an oxygen generating device 4, which comprises an oxygen generator and a first pressure controller. The oxygen generator generates oxygen and has an oxygen outlet. The oxygen outlet communicates with the primary airbag 1 through a first air inlet line 5, and supplies oxygen into the primary airbag 1. In the present disclosure, the oxygen generator is not limited in term of the principle for generating oxygen and the model of the oxygen generator. For example, various oxygen generators which operate on basis of a molecular sieve, a polymer oxygen-enriching membrane, electrolysis of water, or chemical reaction for generating oxygen, fall within the scope of the present disclosure. For example, the present disclosure, a molecular sieve oxygen generating device is adopted. The molecular sieve oxygen generator is the only proven oxygen generator which has both an international standard and a national standard. In the present disclosure, a closeable opening is arranged at an end of the primary airbag 1, the primary airbag 1 is connected with the oxygen generating device 4 through a gas line, and a gas filtering device is arranged in the gas line. As a result, the resultant localized topical hyperbaric therapeutic instrument is an all-in-one machine, which not only generates oxygen, but also provides oxygen treatment. The localized topical hyperbaric therapeutic instrument is not necessary to be equipped with an additional oxygen tank 9, so that it is more convenient and safe to use and carry. In addition, the presently disclosed oxygen generating device can be replaced by an oxygen storage or supply apparatus which supplies oxygen to the primary airbag.

The first pressure controller controls an amount of oxygen supplied to the primary airbag by the oxygen generator, and keeps a value of gas pressure in the primary airbag in a range of 1 KPa-10 KPa. It has been experimentally and clinically proved that in this range of pressure, more effective oxygen therapeutic effects can be delivered. Further, when the value of pressure in the primary airbag 1 is kept in 2 KPa-5 KPa, the oxygen therapeutic effects are much better. Especially when the value of pressure is 3 KPa, the best oxygen therapeutic effects can be obtained. It has been experimentally and clinically found that in this pressure range, the hyperbaric oxygen can sufficiently disperse into tissue cells from the naked wound, so as to provide oxygen for anoxic tissue cells, facilitate proliferation of fibrocyte and generation of collagen matrix, facilitate proliferation of tissue cells, inhibit growth of or even kill anaerobic bacteria in deep wound, reduce generation of extracellular toxin, and accelerate the rehabilitation of the disease. Pressure beyond the above range cannot provide effective therapeutic effects.

The localized topical hyperbaric therapeutic instrument further comprises a massage device 17. The massage device 17 comprises a massage airbag, an air pump (the air compressing device 6) and a second pressure controller. The massage airbag is arranged on an inner wall of the primary airbag 1, the air pump (the air compressing device 6) communicates with the massage airbag 17 through a second air line 8, and the second pressure controller is connected with the air pump (the air compressing device 6) and the massage airbag, respectively, so that the value of gas pressure in the massage airbag 17 changes regularly between 0 and 20 KPa.

The localized topical hyperbaric therapeutic instrument further comprises a heating piece 28, which is arranged in the primary airbag 1 and generates heat, and a treatment unit 29, which is arranged in the primary airbag in a detachable manner at a position corresponding to the heating piece 28. The treatment unit 29 comprises medical ingredients which are volatile upon heating. The heating piece 28 and the treatment unit 29 can be arranged on a bottom or inner wall of the primary airbag, or at a position according to actual need to provide specific therapeutic effects.

In the localized topical hyperbaric therapeutic instrument, the first pressure controller comprises: a first pressure sensor 16, which detects a value of pressure in the primary airbag 1; a first pressure controller 101, which is connected with the first pressure sensor, and receives a signal from the first pressure sensor 16; a first one-way solenoid valve 15, which is arranged in the first air inlet line 5 communicating the oxygen generator with the primary airbag, and prevents oxygen backflow. The primary airbag 1 is provided with an air outlet, which discharges redundant oxygen in the primary airbag 1, to modify the value of pressure in the primary airbag 1. The first one-way solenoid valve 15 is connected with the first pressure controller 101, and as a response to the received signal, the first pressure controller 101 further controls opening and closing of the first one-way solenoid valve 15. The first pressure controller further comprises a venting system, which comprises an exhaust pipe communicating with the primary airbag 1 and a second one-way solenoid valve arranged in the exhaust pipe, the second one-way solenoid valve 24 is connected with the first pressure controller, and as a response to the received signal, the first pressure controller further controls opening and closing of the second one-way solenoid valve. Besides, the air outlet of the primary airbag 1 is further provided with a solenoid valve, which is connected with the first pressure sensor 16 to regulate the value of pressure in the primary airbag 1.

In the localized topical hyperbaric therapeutic instrument, the second pressure controller comprises: a second pressure sensor, which detects a value of pressure in the massage airbag 17; a second pressure controller 102, which is connected with the second pressure sensor, and receives a signal from the second pressure sensor; a two-way solenoid valve 22, which is arranged in the second air line communicating the air pump (the air compressing device 6) and the massage airbag. The two-way solenoid valve 22 is connected with the second pressure controller 102. The second pressure controller 102 responds to the received signal, and controls the two-way solenoid valve 22 to inflate or vent the massage airbag 17. The two-way solenoid valve 22 inflates the massage airbag 17 when it is energized, and stops inflating when it is de-energized, i.e., the air in the massage airbag 17 is discharged.

Figures 3, 4:
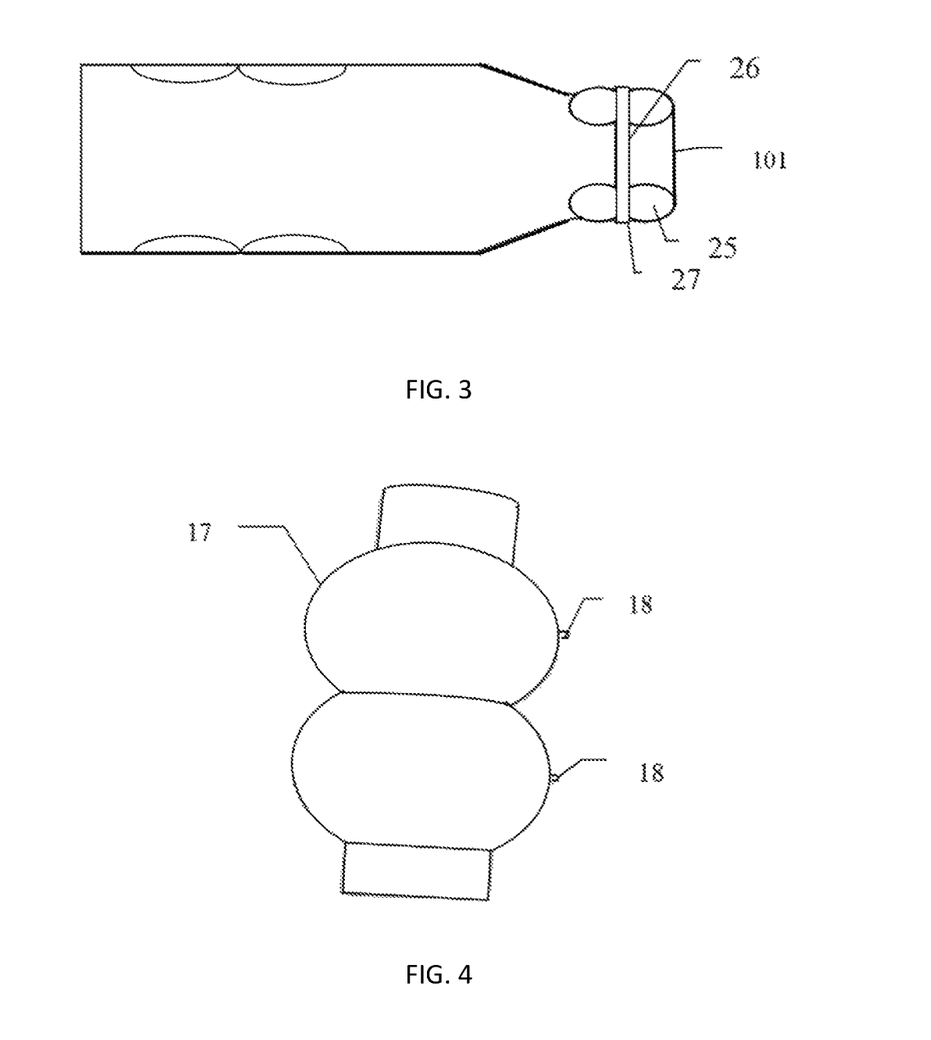
FIG. 3 is a structural view illustrating a sealing part at an opening in a primary airbag of the present disclosure.
FIG. 4 is a structural view illustrating a massage airbag of the present disclosure in an inflated state.
Figure 5:
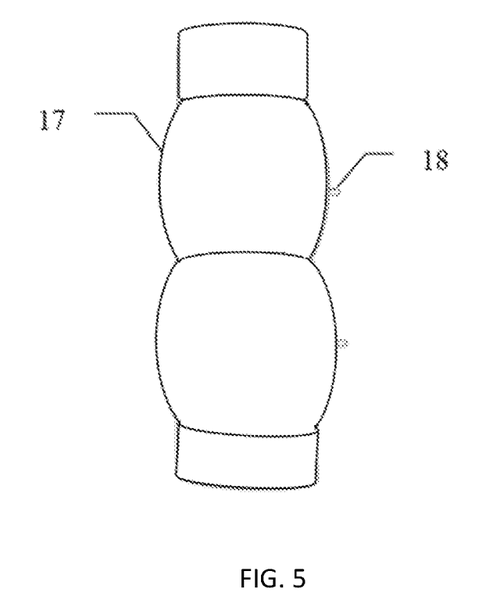
FIG. 5 is a structural view illustrating a massage airbag of the present disclosure in a deflated state.

In the localized topical hyperbaric therapeutic instrument, the massage airbag has a ring shape; the massage airbag 17 has a number of 2 or more, a plurality of the massage airbags along the extending direction of the height of the primary airbag are arranged in parallel. The massage airbag 17 can be arranged as an individual component to provide individual massage. Alternatively, the massage airbag 17 can be arranged on an inner wall of the oxygen treatment airbag, and arranged in parallel along the height direction of the primary airbag 1, so as to be combined with the primary airbag 1 integrally. The massage airbag 17 and a molecular sieve absorption column 7 are connected in a parallel manner in a second air inlet line 8. In particular, they are connected through a T-branch pipe. The second air inlet line 8 passes a heat radiator 12 and then communicates with an orifice of the T-branch pipe, the remaining two orifices of the T-branch pipe are connected with an air inlet 18 of the massage airbag and a gas line to the molecular sieve absorption column 7, respectively. As a result, after air is compressed by an air compressing device 6 and cooled, a portion of the air enters the massage airbag 17, and the remaining portion enters the molecular sieve absorption column 7 for providing oxygen. A second gas flux limiter 19 is arranged in a connecting passage the massage airbag 17 and the second air inlet line 8, for appropriately reducing the portion of air entering the massage airbag 17, and ensuring the majority of air to enter the molecular sieve absorption column 7 for generating oxygen. In the topical hyperbaric oxygen therapeutic instrument of an all-in-one machine type, the connecting passage between the heat radiator 12 and the molecular sieve absorption column 7 is provided with the exhaust pipe and the two-way solenoid valve 22. The exhaust pipe communicates with the two-way solenoid valve 22 for discharging the remaining gas in the molecular sieve absorption column 7.

In the localized topical hyperbaric therapeutic instrument, the oxygen generator is a molecular sieve oxygen generating device. The molecular sieve oxygen generating device comprises the air compressing device 6. At an air inlet end 1001 of the air compressing device 6, an air filtering device 10 is provided for filtering air entering the air compressing device 6. The air filtering device 10 can be a multi-stage filter structure. In the present disclosure, the air filtering device 10 is a two-stage air filter mesh which is arranged in the air inlet line, which filter large particle impurities and small particle impurities in the air respectively, to ensure purity of the air entering the second air inlet line 8. Zeolite is arranged in the molecular sieve absorption column 7. The molecular sieve absorption column 7 is not limited in term of number, and the number can be set to one or more according to actual need. In the present embodiment, the number of the molecular sieve absorption column 7 is two. In case there are molecular sieve absorption columns 7, they are arranged in parallel. The air compressing device 6 communicates with an air inlet 901 of the molecular sieve absorption column 7 through the second air inlet line 8. The second air inlet line 8 is provided with the heat radiator 12 for cooling the air passing through the air compressing device 6. A second one-way valve 23 is arranged in the connecting passage between the air compressing device 6 and the heat radiator 12 for preventing air backflow.

The molecular sieve oxygen generating device further comprises an oxygen tank 9, which communicates with an air outlet 702 of the molecular sieve absorption column 7, and receives and stores oxygen generated by the molecular sieve absorption column 7. The oxygen outlet 901 is arranged in the oxygen tank 9. The oxygen tank 9 is used for temporarily accommodating the generated oxygen. A pressure sensor is arranged inside the oxygen tank 9 for timely displaying the pressure in the oxygen tank 9, so that the pressure is controlled in a safe range. An oxygen filtering device 11 is arranged in the first air inlet line 5 communicating the oxygen outlet 901 and the primary airbag, for filtering oxygen entering the primary airbag through the oxygen outlet, so that the oxygen entering the primary airbag 1 is clean and sterile for safe treatment. The oxygen filtering device 11 can also be a multi-stage filtering system, for further filtering oxygen entering the primary airbag 1 in a stage by stage manner, so that the oxygen is sterile. The multi-stage filtering system can comprise a mesh with dense mesh openings, and a germ filter which is sufficient to filter harmful microbes (e.g., germ) in the air.

The localized topical hyperbaric therapeutic instrument further comprises an oxygen inhaling device 13. The oxygen inhaling device 13 and the primary airbag communicate with the oxygen outlet or the first air inlet line 5 in a parallel manner, respectively. In particular, they can be connected through a T-branch pipe. An orifice of the T-branch pipe communicates with the oxygen outlet, and the remaining two orifices are connected with the oxygen inhaling device 13 and the primary airbag 1, respectively, so that the oxygen inhaling device 13 is parallel with the primary airbag 1. As a result, the therapeutic instrument of an all-in-one machine type not only has the function of oxygen treatment, but also has the function of oxygen inhalation. The T-branch pipe between the oxygen tank 9 and the first air inlet line 5 is provided with a third one-way solenoid valve 24, for preventing oxygen backflow. The connecting passage between the oxygen inhaling device 13 and the oxygen outlet or the first air inlet line 5 is provided with a first gas flux limiter 14, which can limit flux of oxygen entering the oxygen inhaling device 13. As a result, in case the oxygen inhaling device 13 and the primary airbag 1 are used at the same time, it is ensured that most oxygen enters the primary airbag 1, for ensuring a preset value of pressure in the primary airbag 1. A flowmeter can monitor the flux of oxygen in the gas line. In addition, the oxygen inhaling device 13 further comprises a humidifier 131 for humidifying oxygen in the gas line. The humidifier 131 comprises a gas port, to which an oxygen inhalation mask of the oxygen inhaling device 13 can be connected for oxygen inhalation.

In the localized topical hyperbaric therapeutic instrument, the treatment unit 29 comprises an extract tablet and a fixing part 30. The extract tablet is arranged on a side of the heating piece 28 close to the user's skin in a detachable manner through the fixing part 30. In addition, the extract tablet comprises Chinese herbs extract. The Chinese herbs extract is extracted from Chinese herbs composition with an effect of promoting circulation and removing stasis. The Chinese herbs composition comprises the following ingredients in weight parts: Antongteng CAULIS CISSI 5-8 parts by weight, fiveleaf akebia fruit 8-12 parts by weight, Spreading Hedyotis Herb 5-8 parts by weight, Imperata cylindrica root 8-10 parts by weight, Angelica dahurica 8-10 parts by weight, Lobelia chinensis Lour 9-12 parts by weight, Liquidambar formosana Hance infructescence 6-8 parts by weight, myrrh 8-12 parts by weight, caulis sargentodoxae 8-10 parts by weight, Salvia miltiorrhiza 5-8 parts by weight, Rhodiola rosea 8-12 parts by weight, Caulis Spatholobi 8-10 parts by weight, Anoectochilus roxburghii 2-4 parts by weight, radix ranunculi ternati 2-4 parts by weight, flower buds of Radix Notoginseng 5-8 parts by weight, Garden Balsam Stem 8-12 parts by weight, Leonurus japonicus 8-10 parts by weight, pearl barley kernel 8-12 parts by weight, dandelion 8-12 parts by weight and brazilwood 8-12 parts by weight. Antongteng CAULIS CISSI has the effect of relieving rheumatic pains, causing muscles and joints to relax, and detumescence. Fiveleaf akebia fruit has the effect of invigorating circulation of blood, dissipating blood stasis and relieving pain. Spreading Hedyotis Herb has the effect of clearing away heat and toxic material, relieving pain, and promoting urination for removing dampness. Imperata cylindrica root has the effect of cooling blood to stop bleeding, reducing fever and causing diuresis. Angelica dahurica has the effect of dispelling pathogenic wind and removing dampness, and relieving pain. Lobelia chinensis Lour has the effect of clearing away heat and toxic material, and detumescence. Liquidambar formosana Hance infructescence has the effect of relieving rheumatic pains, and stimulating the menstrual flow. Myrrh has the effect of eliminating stasis to activate blood circulation, detumescence, and promoting granulation. Caulis sargentodoxae has the effect of clearing away heat and toxic material, invigorating circulation of blood, relieving rheumatic pain. Salvia miltiorrhiza has the effect of invigorating circulation of blood, cooling blood, and eliminating pain. Rhodiola rosea has the effect of eliminating blood stasis, detumescence, and detoxification. Caulis Spatholobi has the effect of enriching the blood, invigorating circulation of blood, and causing muscles and joints to relax. Anoectochilus roxburghii has the effect of eliminating pathogenic heat from the blood, detumescence, and detoxification. Radix ranunculi ternati has the effect of reducing phlegm and resolving masses. Flower buds of Radix Notoginseng have the effect of invigorating circulation of blood, and detumescence. Garden Balsam Stem has the effect of promoting circulation and removing stasis, detoxifcation, and stimulating the menstrual flow. Leonurus japonicus has the effect of invigorating circulation of blood, and clearing away heat and toxic material. Pearl barley kernel has the effect of detumescence, relaxing the sinews, and clearing away heat and toxic material. Dandelion has the effect of clearing away heat and toxic material, and detumescence. Brazilwood has the effect of invigorating circulation of blood, and detumescence.

In the localized topical hyperbaric therapeutic instrument, the heating piece 28 is a far infrared heating piece. The fixing part 30 comprises a panel and a connecting part. The panel has a mesh shape, and sticking hooks are arranged at crossings of the mesh. The panel has a curved surface with an adjustable curvature, and silica gel bumps with a height of 2-10 mm are arranged around the panel, for avoiding the extract tablet from directly contacting the user's skin. The connecting part fixes the panel in the primary airbag 1, and has an adjustable length, so that an inner side of the panel is spaced apart from the user's skin by 5-15 mm. In use, the extract tablet is fixed by sticking hook in the panel, and the curvature of the panel is modified so as to correspond to the surface of user's limb. The length of the connecting part is modified, so that the distance between the panel and the heating piece 28 (and the user's skin) is modified. Once the power supply of the far infrared heating piece is turned on, the heating piece generates heat, which facilitates volatilizing the Chinese herbs composition in the extract tablet, and provides effects of thermal therapy and medicine fumigation.

In the localized topical hyperbaric therapeutic instrument, the primary airbag 1 is made from a flexible airtight material. The sealing part at the opening 101 of the primary airbag comprises a first elastic sealing ring which is arranged on the inner wall of the opening 101 of the primary airbag 1, and a second elastic sealing ring which is arranged outside the opening 101 of the primary airbag 1. The first elastic sealing ring is hollow, has a width of 3-10 cm, and expands in volume in an inflated state to decrease inner diameters of the elastic sealing rings. One or more annular groove is arranged on the surface of the first elastic sealing ring 25 in the inflated state. The second elastic sealing ring 26 is arranged outside the opening 101 of the primary airbag 1, and is embedded in the annular groove of the first elastic sealing ring 25, so that the opening 101 of the primary airbag 1 is shrunken and sealed. After the user get his local limb into the primary airbag 1, the first elastic sealing ring 25 is inflated, the first elastic sealing ring expands, and the bore decrease to wrap the user's limb. The second elastic sealing ring 26 is embedded in the annular groove 27 of the first elastic sealing ring 25 outside the opening 101 of the primary airbag 1, and is tightened to close fit to the first elastic sealing ring 25. This significantly improves sealing performance of the primary airbag 1, thus facilitating that an effective pressure is reached and kept in the primary airbag.

The localized topical hyperbaric therapeutic instrument further comprises: a box 31, in which the oxygen generating device 4 and the air pump (the air compressing device 6) are arranged; a control panel, which is provided with a control circuit and a control button, wherein the control panel is arranged in the box 31, and the first pressure controller and the second pressure controller are connected with the control circuit of the control panel, respectively; a buzzer and timer, which is connected with the control panel. The control panel is further provided with a mode switch button and a switching intensity button. The control circuit receives operating instructions from the user to control switching on and off each component in the topical hyperbaric oxygen therapeutic instrument of an all-in-one machine type, and automatically controls opening and closing of each of the one-way solenoid valve and two-way solenoid valve by monitoring data detected by the pressure sensor, so as to automatically regulate pressure in the primary airbag 1, pressure in the massage airbag 17, and flux of the oxygen inhaling device 13. By controlling the air compressing device 6, the control circuit can generate two air fluxes, which are applicable to different actual needs. By monitoring the data detected by the oxygen tank 9, the control circuit controls the two-way solenoid valve 22. When the pressure reaches a maximum value, the control circuit closes the two-way solenoid valve 22 to protect the gas line.

Embodiment 1

The leg is put into the opening of the primary airbag 1, and the opening is tightened and sealed with a rubber band.

Firstly, the switching intensity button and the mode switch button are pressed to start the instrument and select the massage intensity. Once the indicator lamp of the power supply is on, the switching button is pressed to select "oxygen treatment mode" (in which only the primary airbag 1 is inflated and deflated), "massage mode" (in which the massage airbag 17 is inflated and deflated) or "oxygen inhalation mode" (oxygen inhalation through an oxygen mask which is connected outside the air outlet of the humidifier 131).

In implementations, in case "oxygen treatment mode" is selected, the control circuit sends a signal for switching on the air compressing device 6, the first, second and third one-way solenoid valve 24, the two-way solenoid valve 22. The air sequentially passes through the air filtering device 10, the air compressing device 6, and the heat radiator 12 to enter the molecular sieve absorption column 7 of the oxygen generating device 4. The separated oxygen enters the oxygen tank 9 and enters the primary airbag 1 through the oxygen filtering device 11. The redundant oxygen is discharged through the air outlet of the primary airbag 1. After one minute, the control circuit sends a signal to close the air outlet of the primary airbag 1. The first pressure sensor 16 sends a detection signal to the control circuit. When the oxygen pressure reaches the preset pressure of 1-10 KPa, the control circuit sends a signal to close the first one-way solenoid valve 15, and the primary airbag 1 maintains the pressure. When the oxygen pressure exceeds the preset pressure of 10 KPa, the control circuit controls to close the first one-way solenoid valve 15 and controls to discharge redundant oxygen through the air outlet of the primary airbag 1. When the oxygen pressure is lower than the preset pressure of 1 KPa, the control circuit controls to open the first one-way solenoid valve 15 again, the primary airbag 1 is inflated with oxygen through the first one-way solenoid valve 15 again. In this way, the pressure in the primary airbag 1 is kept in the range of 1 KPa-10 KPa during oxygen treatment.

By pressing the switching button of the intensity and mode switching button, "massage mode" is selected. The control circuit sends signal to switch on the air compressing device 6 and the two-way solenoid valve 20. Air enters the massage airbag 17. The second pressure sensor 21 sends a detection signal to the control circuit. When the air pressure reaches the preset pressure, the control circuit controls to switch off the air compressing device 6, and the massage airbag 17 maintains the pressure. After a while, the control circuit sends a control signal, the vent valves in the two-way solenoid valve 20, the air compressing device 6, and the massage airbag 17 are opened, and the massage airbag 17 discharges gas. These are repeated to complete the massage process. When the treatment duration reaches a preset duration, the timer outputs a signal to the control circuit. The air compressing device 6 and various solenoid valves stop operating, the vent valve of the massage airbag 17 is open for deflating, and the massage is complete.

By pressing the switching button of the intensity and mode switching button, "oxygen inhalation mode" is selected. The control circuit sends a signal to switch on the air compressing device 6, the two-way solenoid valve 22, and the third one-way solenoid valve 24. The first gas flux limiter 14 is modified to a value set by the user, and the user can perform oxygen inhalation through an oxygen mask which is connected to the air outlet of the humidifier 131.

The above are merely embodiments of the present disclosure. It should be appreciated that, a person skilled in the art may make further improvements and modifications without departing from the principle of the present disclosure, and these improvements and modifications shall also fall within the scope of the present disclosure.

What is claimed is:

1. A localized topical hyperbaric therapeutic instrument, comprising:

a primary airbag (1), which is a chamber with an opening (101) at an end, wherein the opening is provided with a sealing part (2);

an oxygen generating device (4), which comprises an oxygen generator and a first pressure controller (101), wherein the oxygen generator generates oxygen and has an oxygen outlet, and the oxygen outlet communicates with the primary airbag (1) through a first air inlet line (5) and supplies oxygen into the primary airbag (1), and wherein the first pressure controller (101) controls an amount of oxygen supplied to the primary airbag (1) by the oxygen generator, and keeps a value of gas pressure in the primary airbag (1) in a range of 1 KPa-10 KPa; the oxygen generator comprises a molecular sieve absorption column (7) and an oxygen tank (9); the first pressure controller (101) comprises a first pressure sensor (16) and a first one-way solenoid valve (15);

a massage device, which comprises a massage airbag (17), an air compressing device (6) and a second pressure controller (102), wherein the massage airbag (17) is arranged on an inner wall of the primary airbag, the air compressing device (6) communicates with the massage airbag through a second air line (8), and the second pressure controller (102) is connected with the air compressing device (6) and the massage airbag (1), respectively, so that the value of gas pressure in the massage airbag changes regularly between 0 and 20 KPa; the second pressure controller (102) comprises a second pressure sensor (21) and a second one-way solenoid valve (24);

a heating piece (28), which is arranged in the primary airbag (1) and generates heat; and a treatment unit (29), which is arranged in the primary airbag (1) in a detachable manner, disposed at a position corresponding to the heating piece, and comprises medical ingredients which are volatile upon heating.

2. The localized topical hyperbaric therapeutic instrument of claim 1, wherein the first pressure sensor 16 detects a value of pressure in the primary airbag (1);

the first pressure controller is connected with the first pressure sensor (16), and receives a signal from the first pressure sensor (16);

the first one-way solenoid valve (15) is arranged in the first air inlet line communicating the oxygen generator and the primary airbag (1), the first one-way solenoid valve (15) is connected with the first pressure controller, and as a response to the received signal, the first pressure controller further controls opening and closing of the first one-way solenoid valve (15); and a venting system comprises an exhaust pipe communicating with the primary airbag (1) and the second one-way solenoid valve (24) arranged in an exhaust pipe, the second one-way solenoid valve (24) is connected with the first pressure controller, and as a response to the received signal, the first pressure controller further controls opening and closing of the second one-way solenoid valve (24).

3. The localized topical hyperbaric therapeutic instrument of claim 1, wherein the second pressure sensor (21) detects a value of pressure in the massage airbag (17);

the second pressure controller is connected with the second pressure sensor (21), and receives a signal from the second pressure sensor (21); and a two-way solenoid valve (22) is arranged in the second air line (8) communicating the air compressing device (6) and the massage airbag (1), the two-way solenoid valve (22) is connected with the second pressure controller, and as a response to the received signal, the second pressure controller controls the two-way solenoid valve (22) to inflate or vent the massage airbag (1).

4. The localized topical hyperbaric therapeutic instrument of claim 1, wherein the massage airbag (1) has a ring shape, the localized topical hyperbaric therapeutic instrument has two or more massage airbags, and the massage airbags in parallel are arranged along the extending direction of the height of the primary airbags.

5. The localized topical hyperbaric therapeutic instrument of claim 1, wherein the oxygen generating device is a molecular sieve oxygen generating device, and the molecular sieve oxygen generating device comprises:

the air compressing device (6), wherein an air filtering device (10) is arranged at an air inlet end (701) of the air compressing device (6), for filtering the air which enters the air compressing device;

the molecular sieve absorption column (7), wherein the air compressing device communicates with an air inlet (701) of the molecular sieve absorption column (7) through a second air inlet line (8), and a heat radiator (12) is arranged in the second air inlet line (8); and the oxygen tank (9), wherein the oxygen tank (9) communicates with an air outlet (702) of the molecular sieve absorption column (7), and receives and stores the oxygen generated by the molecular sieve absorption column (7); wherein the oxygen outlet (901) is arranged in the oxygen tank (9); wherein an oxygen filtering device (11) is arranged in the first air inlet line (5) which communicates the oxygen outlet (901) and the primary airbag (1), for filtering the oxygen which enters the primary airbag (1) through the oxygen outlet (901).

6. The localized topical hyperbaric therapeutic instrument of claim 5, further comprising an oxygen inhaling device (13), wherein the oxygen inhaling device (13) and the primary airbag (1) communicate in a parallel manner with the oxygen outlet (901) or the first air inlet line (5), respectively;

a first gas flux limiter (14) is arranged in a connecting passage between the oxygen inhaling device (13) and the oxygen outlet (901) or the first air inlet line (5).

7. The localized topical hyperbaric therapeutic instrument of claim 1, wherein the treatment unit (29) comprises an extract tablet (291) and a fixing part (30), the extract tablet (291) is arranged on a side of the heating piece (28) close to the user's skin in a detachable manner through the fixing part; and the extract tablet comprises Chinese herbs extract which is extracted from a Chinese herbs composition with an effect of promoting circulation and removing stasis, and the Chinese herbs composition comprises the following ingredients:

5-8 parts of antongteng CAULIS CISSI, 8-12 parts of fiveleaf akebia fruit, 5-8 parts of Spreading Hedyotis Herb, 8-10 parts of Imperata cylindrica root, 8-10 parts of Angelica dahurica, 9-12 parts of Lobelia chinensis Lour, 6-8 parts of Liquidambar formosana Hance infructescence, 8-12 parts of myrrh, 8-10 parts of caulis sargentodoxae, 5-8 parts of Salvia miltiorrhiza, 8-12 parts of Rhodiola rosea, 8-10 parts of Caulis Spatholobi, 2-4 parts of Anoectochilus roxburghii, 2-4 parts of radix ranunculi ternati, 5-8 parts of flower buds of Radix Notoginseng, 8-12 parts of Garden Balsam Stem, 8-10 parts of Leonurus japonicus, 8-12 parts of pearl barley kernel, 8-12 parts of dandelion, and 8-12 parts of brazilwood by weight.

8. The localized topical hyperbaric therapeutic instrument of claim 7, wherein the heating piece (28) is a far infrared heating piece; and wherein the fixing part (30) comprises:

a panel (301) that has a mesh, wherein sticking hooks (302) are arranged at crossings of the mesh, the panel has a curved surface (303) with an adjustable curvature, and silica gel bumps (304) with a height of 2-10 mm are arranged around the panel; and a connecting part (305), wherein the connecting part (305) fixes the panel in the primary airbag (1), and the connecting part (305) has an adjustable length, so that an inner side of the panel is spaced apart from the user's skin by 5-15 mm.

9. The localized topical hyperbaric therapeutic instrument of claim 1, wherein the primary airbag (1) is made from a flexible airtight material, the sealing part (2) at the opening of the primary airbag (1) comprises a first elastic sealing ring (25) which is arranged on an inner wall of the primary airbag (1) at the opening, and a second elastic sealing ring (26) which is arranged outside the opening of the primary airbag 1, wherein the first elastic sealing ring (25) is hollow, has a width of 3-10 cm, and expands in volume in an inflated state to decrease inner diameters of the first elastic sealing ring (25), wherein one or more annular groove (27) is arranged on the surface of the first elastic sealing ring (25) in the inflated state; and the second elastic sealing ring (26) is arranged outside the opening of the primary airbag (1), and is embedded in the annular groove (27) of the first elastic sealing ring (25), so that the opening of the primary airbag (1) is shrunken and sealed.

10. The localized topical hyperbaric therapeutic instrument of claim 2, further comprising:

a box (31) in which the oxygen generating device and the compressing device (6) are arranged;

a control panel which is arranged in the box, wherein the first pressure controller and the second pressure controller are connected with the control panel, respectively; and a timer which is connected with the control panel.

11. The localized topical hyperbaric therapeutic instrument of claim 3, further comprising:

a box (31) in which the oxygen generating device and the compressing device (6) are arranged;

a control panel which is arranged in the box, wherein the first pressure controller and the second pressure controller are connected with the control panel, respectively; and a timer which is connected with the control panel.

12. The localized topical hyperbaric therapeutic instrument of claim 4, further comprising:

a box (31) in which the oxygen generating device and the compressing device (6) are arranged;

a control panel which is arranged in the box, wherein the first pressure controller and the second pressure controller are connected with the control panel, respectively; and a timer which is connected with the control panel.

13. The localized topical hyperbaric therapeutic instrument of claim 6, further comprising:

a box (31) in which the oxygen generating device and the compressing device (6) are arranged;

a control panel which is arranged in the box, wherein the first pressure controller and the second pressure controller are connected with the control panel, respectively; and a timer which is connected with the control panel.

14. The localized topical hyperbaric therapeutic instrument of claim 8, further comprising:

a box (31) in which the oxygen generating device and the air compressing device (6) are arranged;

a control panel which is arranged in the box, wherein the first pressure controller and the second pressure controller are connected with the control panel, respectively; and a timer which is connected with the control panel.

15. The localized topical hyperbaric therapeutic instrument of claim 9, further comprising:

a box (31) in which the oxygen generating device and the air compressing device (6) are arranged;

a control panel which is arranged in the box, wherein the first pressure controller and the second pressure controller are connected with the control panel, respectively; and a timer which is connected with the control panel.

\* \* \* \* \*